(12) United States Patent
Adams

(10) Patent No.: US 8,845,658 B2
(45) Date of Patent: Sep. 30, 2014

(54) HEMOSTATIC CLIP AND DELIVERY SYSTEM

(75) Inventor: Mark L. Adams, Sandy, UT (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1283 days.

(21) Appl. No.: 12/033,449

(22) Filed: Feb. 19, 2008

(65) Prior Publication Data

US 2008/0208217 A1 Aug. 28, 2008

Related U.S. Application Data

(60) Provisional application No. 60/891,579, filed on Feb. 26, 2007.

(51) Int. Cl.
*A61B 17/10* (2006.01)
*A61B 17/122* (2006.01)
*A61B 17/12* (2006.01)
*A61B 17/128* (2006.01)

(52) U.S. Cl.
CPC ......... *A61B 17/12013* (2013.01); *A61B 17/122* (2013.01); *A61B 17/1285* (2013.01)
USPC .......................................... 606/142; 606/157

(58) Field of Classification Search
USPC ........................... 606/142, 139, 153, 157, 158
See application file for complete search history.

(56) References Cited

U.S. PATENT DOCUMENTS

| | | | |
|---|---|---|---|
| 4,589,416 A | 5/1986 | Green | |
| 5,122,136 A | 6/1992 | Guglielmi et al. | |
| 5,306,280 A | 4/1994 | Bregen et al. | |
| 5,354,295 A * | 10/1994 | Guglielmi et al. | 606/32 |
| 5,417,700 A | 5/1995 | Egan | |
| 5,891,128 A | 4/1999 | Gia et al. | |
| 5,908,429 A | 6/1999 | Yoon | |
| 5,972,004 A | 10/1999 | Williamson, IV et al. | |
| 6,432,128 B1 | 8/2002 | Wallace et al. | |
| 6,491,707 B2 | 12/2002 | Makower et al. | |
| 6,699,255 B1 | 3/2004 | Cushchieri et al. | |
| 6,709,442 B2 * | 3/2004 | Miller et al. | 606/153 |
| 6,749,622 B2 | 6/2004 | McGuckin, Jr. et al. | |
| 2002/0128667 A1 | 9/2002 | Kobayashi et al. | |

(Continued)

FOREIGN PATENT DOCUMENTS

| | | |
|---|---|---|
| EP | 1 011 520 | 6/2000 |
| JP | 63267345 | 11/1988 |

(Continued)

*Primary Examiner* — Gregory Anderson
(74) *Attorney, Agent, or Firm* — Fay Kaplun & Marcin, LLP

(57) ABSTRACT

A clipping device includes (a) a shaft defining a lumen therethrough from a proximal end which, during a procedure remains outside the body accessible to a user and a distal end including a distal opening which, during a procedure is inserted into the body to a position adjacent to target tissue; (b) a flexible clip deployable from the distal opening, when in an unconstrained state, the clip assuming a shape selected to clip tissue and prevent a flow of fluid therethrough wherein, while residing within the lumen the clip is held substantially straight by an inner diameter of the lumen; (c) a control wire extending through the lumen from the proximal end to the distal end thereof; and (d) a release mechanism connecting the control wire to the clip during deployment of the clip and disconnecting the control wire from the clip after deployment thereof.

18 Claims, 4 Drawing Sheets

AFTER DEPLOYMENT

(56) References Cited

U.S. PATENT DOCUMENTS

| | | |
|---|---|---|
| 2002/0138083 A1 | 9/2002 | Muramatsu et al. |
| 2002/0198592 A1 | 12/2002 | Wallace et al. |
| 2004/0002718 A1 | 1/2004 | Trout, III et al. |
| 2004/0193246 A1 | 9/2004 | Ferrera |
| 2005/0107809 A1 | 5/2005 | Litscher et al. |
| 2005/0203552 A1 | 9/2005 | Laufer et al. |
| 2006/0282112 A1 | 12/2006 | Griffin |

FOREIGN PATENT DOCUMENTS

| | | |
|---|---|---|
| JP | 2000-254143 | 9/2000 |
| WO | 92/05828 | 4/1992 |
| WO | 98/11846 | 3/1998 |
| WO | 00/49973 | 8/2000 |
| WO | 2004/091381 | 10/2004 |
| WO | 2005/070309 | 8/2005 |

\* cited by examiner

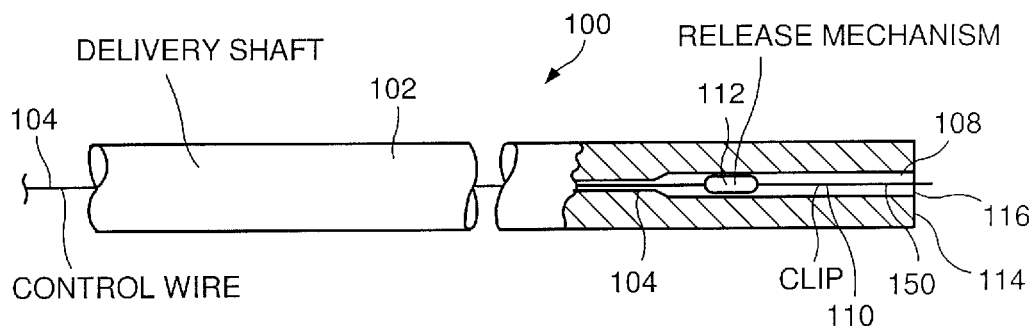
F I G. 1 BEFORE DEPLOYMENT
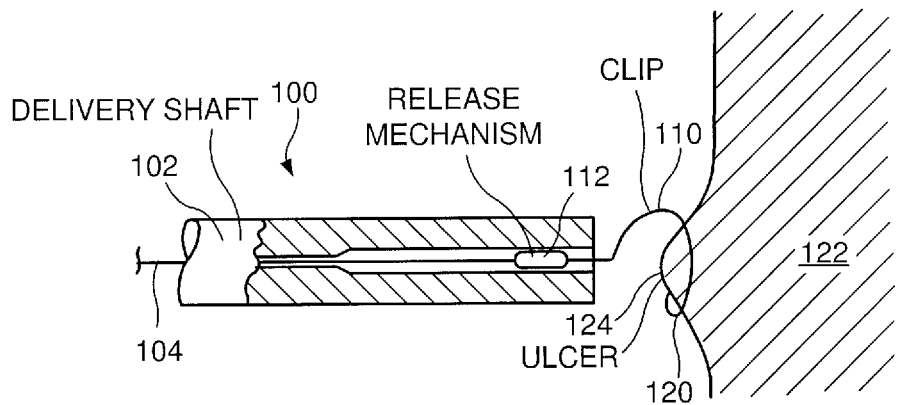
F I G. 2 DURING DEPLOYMENT
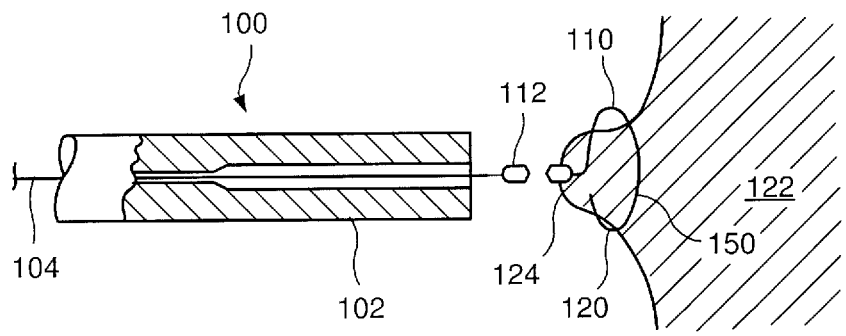
F I G. 3 AFTER DEPLOYMENT

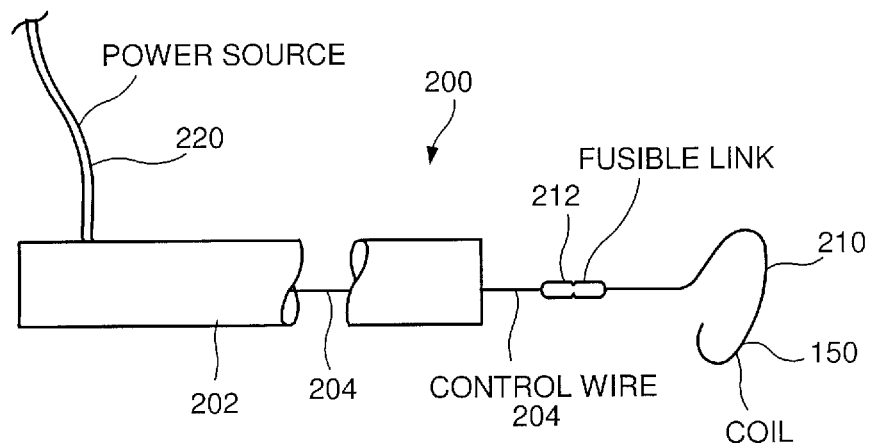
F I G. 4
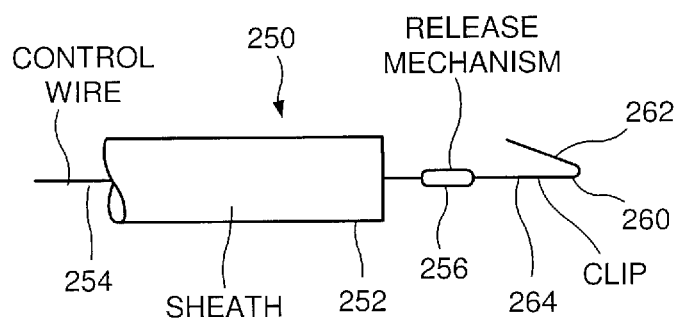
F I G. 5

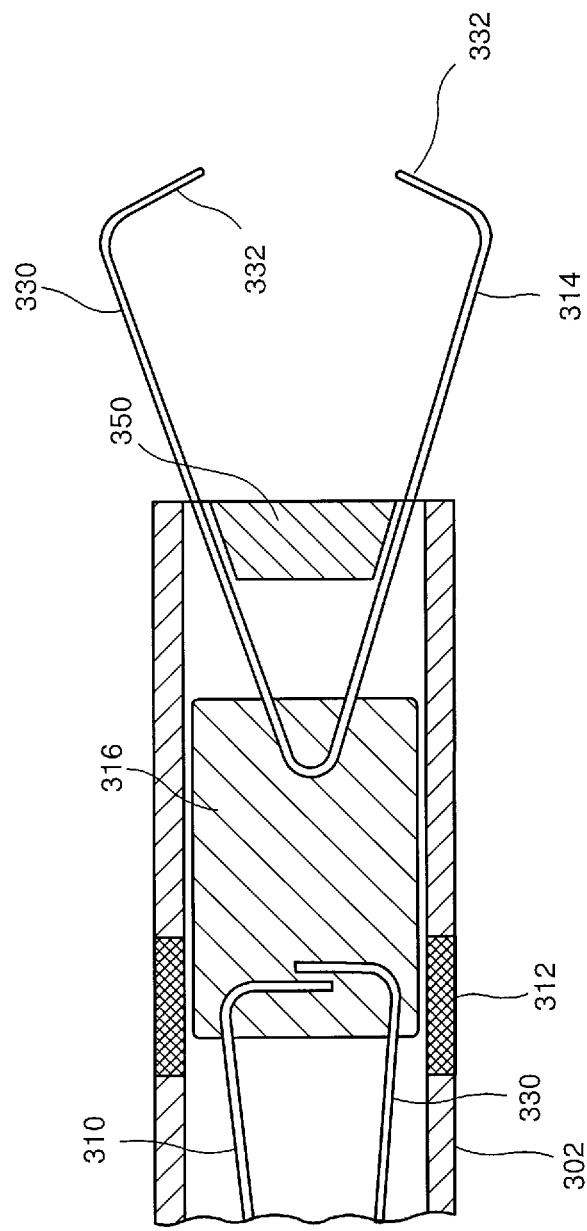
F I G. 7

HEMOSTATIC CLIP AND DELIVERY SYSTEM

PRIORITY CLAIM

This application claims the priority to the U.S. Provisional Application Ser. No. 60/891,579, entitled "Hemostatic Clip and Delivery System," filed Feb. 26, 2007. The disclosure of the above application is expressly incorporated herein, in its entirety, by reference.

BACKGROUND

Peptic ulcer disease (PUD) is a condition where bleeding occurs from the walls of the gastro intestinal (GI) tract. A peptic ulcer is an erosion in the lining of the stomach or duodenum. Symptoms vary from patient to patient and may include nausea, heartburn, fatigue, vomiting blood etc. The condition is particularly dangerous in cases where the lesion to the tissue perforates the lining of the stomach or of the intestine, requiring emergency medical attention.

Treatment for PUD consists of hemostasis procedures, where the flow of blood from the damaged blood vessels is stopped. The procedure may be carried out endoscopically, with thermal therapy, injection of hemostatic medications, or cautery using lasers and argon plasma. Clips and other mechanical devices such as the Endoclip™ devices manufactured by the Olympus Corporation, may also be used to stop the flow of blood from the eroded tissue. Because the location of these hemorrhages are often deep within the body, deploying hemostatic clips is a complex and time consuming procedure.

SUMMARY OF THE INVENTION

The present invention is directed to a clipping device comprising a shaft defining a lumen therethrough from a proximal end which, during a procedure remains outside the body accessible to a user and a distal end including a distal opening which, during a procedure is inserted into the body to a position adjacent to target tissue and a flexible clip deployable from the distal opening, when in an unconstrained state, the clip assuming a shape selected to clip tissue and prevent a flow of fluid therethrough wherein, while residing within the lumen the clip is held substantially straight by an inner diameter of the lumen in combination with a control wire extending through the lumen from the proximal end to the distal end thereof and a release mechanism connecting the control wire to the clip during deployment of the clip and disconnecting the control wire from the clip after deployment thereof.

The invention is further directed to an endoscopic tissue clipping system comprising a shaft sized and shaped for insertion through a working channel of an endoscope and a clip assembly disposable within the distal end of the shaft, the clip assembly comprising a plurality of clips connected to one another by links, each clip being biased toward a closed position selected to clip tissue and a control wire operatively connected to the clip assembly to advance the clip assembly through the clip magazine. The system further includes a heating element disposed on the distal end of the shaft, the heating element being operable to degrade a selected one of the links to release a distal most one of the clips from the clip assembly and a cam selectively opening the distal most clip to receive target tissue so that, after passing the cam, the clip moves to the closed position.

In addition, the invention is directed to a method for clipping tissue comprising advancing a distal end of a flexible shaft to a first desired position within the body adjacent to a first portion of target tissue to be clipped and actuating a control wire extending through the shaft to advance a clip out of the distal end of the shaft over the first portion of target tissue, the clip being biased toward a tissue clipping shape selected to grip tissue received therein wherein, when received within the shaft, the clip is substantially straight in combination with advancing the clip out of the delivery shaft so that the clip reverts to the tissue clipping shape compressing the first portion of target tissue received therein and detaching the clip from the control wire.

BRIEF DESCRIPTION OF DRAWINGS

FIG. 1 shows a diagram of a delivery system for an hemostatic clip according to the invention;

FIG. 2 shows a diagram of the delivery system according to the invention with a clip being deployed;

FIG. 3 shows a diagram of the delivery system shown in FIG. 2 with the clip fully deployed;

FIG. 4 shows a diagram of a second embodiment of a delivery system for an hemostatic clip according to the invention;

FIG. 5 shows a diagram of a third embodiment of a delivery system for an hemostatic clip according to the invention;

FIG. 7 shows a detail of the distal end of the delivery system shown in FIG. 6.

DETAILED DESCRIPTION

Figure 6:
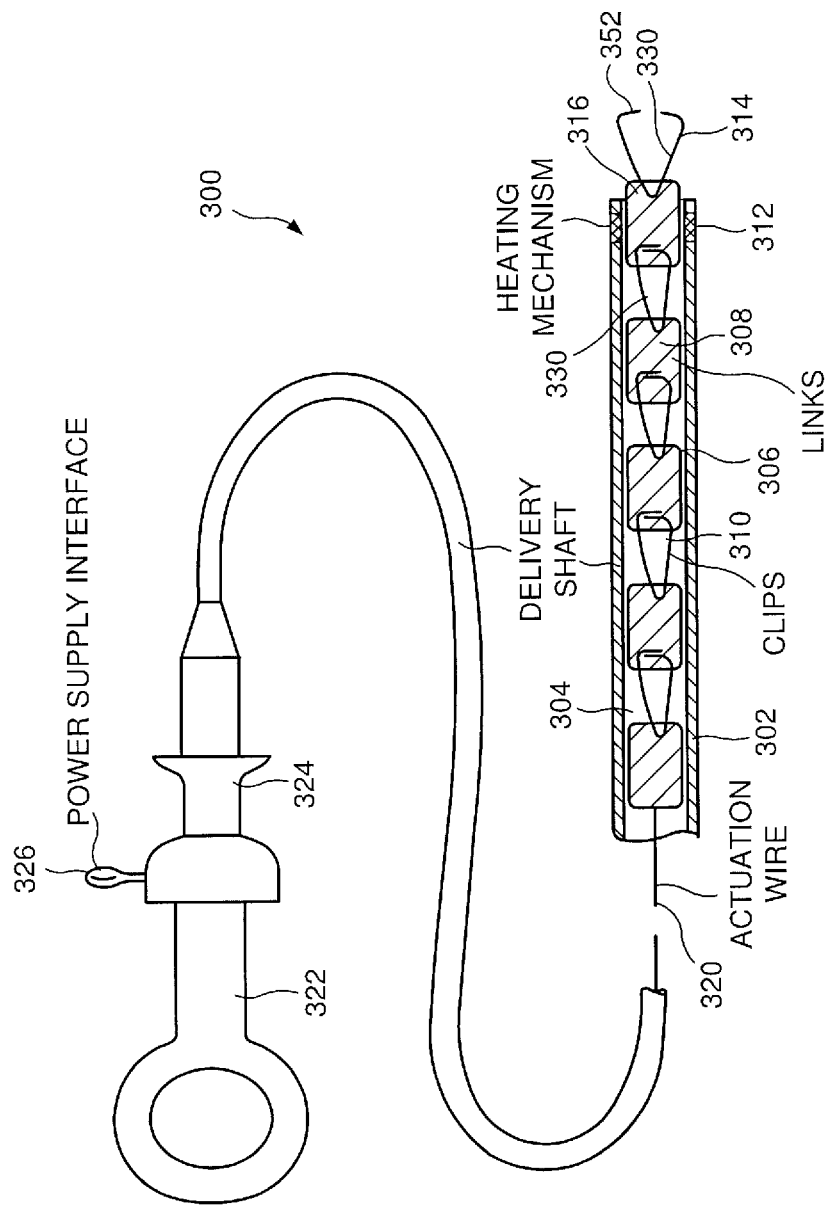
FIG. 6 shows a diagram of a further embodiment of a delivery system according to the present invention, for delivering multiple hemostatic clips.

The present invention may be further understood with reference to the following description and to the appended drawings, wherein like elements are referred to with the same reference numerals. The present invention relates to hemostasis procedures including endoscopic hemostasis procedures. More specifically, the invention relates to systems and methods for delivering hemostatic clips to the GI tract. However, those skilled in the art will understand that the clips according to the invention may be used for procedures other than those directed to hemostasis. For example, the clips may be used to join tissue layers, folds or organs or for grasping tissue for removal or repositioning. The clips may be rotatable through rotation of a control wire coupled thereto. Furthermore, the device according to the present invention may be used in conjunction with a standard endoscope or may alternatively include a vision system of its own. Alternatively, the device may be configured for use with a specialized endoscope and may be delivered without direct visualization using other known techniques to locate the target site as would be understood by those skilled in the art.

The embodiments of the present invention cause hemostasis of bleeding blood vessels in a body lumen (e.g., within the GI tract) using a clip designed to stop the flow of blood to an ulcer or to other target tissue. The exemplary clip according to the invention is formed into the desired shape at the bleeding site, and is not preformed before delivery to the target site. The resulting delivery mechanism may be made smaller and more flexible than current designs making the delivery device more maneuverable and user friendly and facilitating delivery of the delivery mechanism and the clips to target sites via an endoscope.

As will be understood by those skilled in the art, the hemostatic clip system of the present invention may be used to control GI bleeding as well as to stop a flow of fluids elsewhere in the body. For example, the invention may be used to stop bleeding in procedures such as endoscopic mucosal resectomy, bowel perforations, tube ligation closures, etc. Bleeding or other fluid flow located in hard to reach anatomical cavities may be treated using the device according to the invention.

An exemplary embodiment of the hemostatic clip and delivery system according to the invention is shown in FIG. 1. The hemostasis system 100 comprises a delivery sheath or shaft 102, a control wire 104, a release mechanism 112 and a clip 110. The distal end 114 of the delivery sheath 102 is advanced through an endoscope working channel to the target tissue, while a proximal end of the control wire 104 remains accessible to the operator.

The delivery sheath 102 may be, for example, an hollow shaft similar to a catheter or a flexible biopsy forceps. The outside diameter of the delivery sheath 102 may be of approximately 0.100 inches or less. The small diameter allows the shaft to rotate freely within the working channel of an endoscope during use, to assist in placing the clip 110. The delivery sheath 102 may comprise a working channel 108 extending therethrough, to contain the clip 110 and a control wire 104. A distal opening 116 permits deployment of the clip 110 over the target tissue.

In one exemplary embodiment, the delivery sheath 102 may be manufactured of a plastic such as HDPE, or may comprise a metallic core coated with a lubricious outer shell. Alternatively, the delivery sheath 102 may be manufactured of a braid-reinforced polymer to improve its mechanical characteristics. Those of skill in the art will understand that other materials may be used to manufacture the delivery shaft of the present invention.

The exemplary control wire 104 may be metallic, and is used to advance the clip 110 from within the delivery sheath 102. Near the distal end 114 the control wire 104 is operatively connected to the clip 110 via a release mechanism 112, described in greater detail below. The proximal end of the control wire 104 extends beyond the proximal end of the delivery sheath 102 to connect to an actuating mechanism used by the operator to release the clip 110.

The release mechanism 112 provides an interface between the control wire 104 and the clip 110 forming a mechanical connection to the clip 110 while the device is inserted into the body and during the initial steps of deployment of the clip 110. In the final stages of deployment, the release mechanism 112 severs the mechanical connection so that the clip 110 remains attached to the target tissue and the delivery sheath 102 can be withdrawn.

In one exemplary embodiment, the release mechanism 112 comprises a weakened, failure point of the control wire 104 having, for example, a cross sectional area reduced compared to the rest of the control wire 104. An end of the control wire 104, distal from the release mechanism 112, may be attached to the clip 110 with conventional means, such as welding, soldering, heat shrink, etc. When it is necessary to release the clip 110 from the control wire 104, force is applied to the release mechanism 112 to break the mechanical connection. For example, a torsional shear force may be applied through the control wire 104 from the proximal end, sufficient to cause the failure point to fail.

In a different embodiment of the release mechanism 112, a polymer or other bonding agent may be used to bond a proximal portion of the coil 110 to a distal portion thereof with a torsional shear strength of the polymer selected to be lower than that of the rest of the control wire 104 to define a failure point where the proximal and distal portions are bonded to one another. After a coil 110 has been secured to target tissue, the control wire 104 is twisted by the user imparting to the failure point a torque shear which, when a predetermined level is exceeded, causes the failure point to yield separating the proximal and distal portions of the control wire 104 from one another.

In another embodiment, the release mechanism 112 may comprise a fusible link coupled to an electrically conductive control wire. The exemplary delivery system 200 shown in FIG. 4 comprises a delivery sheath 202 with a conductive control wire 204 passing therethrough. A fusible link 212 connects the control wire 204 to the clip 210 before deployment is complete. When it is desired to separate the clip 210 from the control wire 204, electric current sufficient to cause failure of the fusible link is supplied to the control wire 204 releasing the clip 210 from the control wire 204. For example, as would be understood by those skilled in the art, the capacitance of the fusible link 212 may be selected to be less than that of the control wire 204 so that, when electric current is applied to the control wire 204 from the power source 220, the fusible link 212 melts or breaks severing the bond between the control wire 204 and the clip 210.

The exemplary delivery system 100 shown in FIG. 1 also includes a clip 110 comprising, for example, a coil which returns to a desired shape after deformation. As would be understood by those skilled in the art, the coil forming the clip 110 may be made from a preformed metallic wire 150, or from any other material having the desired mechanical and elastic properties. In its natural, unconstrained state the wire 150 has the shape of a loop, as shown by clips 110 and 210 in FIGS. 3 and 4. When the coil 110 is assembled within the delivery sheath 102, the shape of the working channel 108 forces it into a substantially straight shape, as shown in FIG. 1. Thus, when inside the delivery sheath 102, the coil 110 appears as a substantially straight wire.

Once the target tissue is reached, the coil 110 is advanced by the control wire 104 through the opening 116, such that the constraining force is removed. The coil 110 then takes its natural, unrestricted loop shape, and coils around the target tissue to compress it and mechanically cause hemostasis. This condition is shown in FIG. 3. Those of skill in the art will understand that various materials may be used to manufacture the coil 110. For example, shape memory alloys or other materials that are capable of assuming a desired shape in response to changes in external conditions may be used. Any materials or coatings that strengthen the clip without adding large amounts of material and increasing the cross sectional dimension of the clip may be used.

An alternative embodiment of the hemostatic clip according to the invention is shown in FIG. 5. In this embodiment, the clip 260 of the delivery system 250 has an operative shape resembling the letter "V", similar to the shape of a surgical clip or an aneurysm clip. Prior to deployment, the clip 260 is contained within the deployment sheath 252 in the shape of a substantially straight wire. When the control wire 254 pushes it out, the clip 260 returns to the unconstrained "V" shape configuration, with legs 262, 264 joined at a sharp bend. The clip 260 is placed over the target tissue before returning to the unconstrained shape, so that the release mechanism 256 can detach the clip and leave it on the target tissue.

An exemplary mode of use of the hemostatic clip deployment system is described with reference to FIGS. 1-3. The preliminary steps of intubating the patient, insufflating and locating the bleeding site with an endoscope are carried out. The delivery device 100 is introduced into the scope and is advanced to the site, in proximity of the target tissue 122. Specifically, the distal tip of the delivery sheath 102 is placed against an ulcer 124 or other opening to be closed (e.g., wounds resulting from biopsies, polyp removal, etc.). The procedure may be controlled visually by the physician using the vision equipment of an endoscope.

The control wire 104 is advanced through the working channel 108, thus advancing the coil 110 out of the opening 116 of the delivery sheath 102 and onto the ulcer 124. Under direct visualization, the clip 110 continues to be advanced and, as it leaves the delivery sheath 102, it forms a tightening coil 120 around the ulcer 124. The base of the ulcer 124 is compressed, stopping the flow of blood to the wound. When the coil 120 is fully formed, the physician twists the control wire 104 to break the release mechanism 112. Twisting the control wire 104 may also plastically deform the coil 120, applying additional force to the lesion aiding in establishing hemostasis. The delivery sheath 102 may then be withdrawn while leaving the clip 110 coiled around the ulcer 124.

In many cases the ulcer is large, and more than one clip may be necessary to completely close the wound and stop the hemorrhage. Placing multiple clips on the target tissue may be difficult with a single clip device, because it is necessary to remove the device, load an additional clip and advance the device again to the correct site of the lesion to deploy the new clip. Multi-clip devices may be used, which store multiple clips and are able to deploy them on the lesion without needing to remove, reload and reintroduce the device to target site.

Embodiments of the present invention provide for a multi-clip delivery device to cause hemostasis of hemorrhaging blood vessels that are difficult to reach. In particular, the treatment of bleeding occurring along the GI tract such as peptic ulcers may be treated by deploying multiple clips with the invention, which may be delivered to the target site of the bleeding with an endoscope.

In one embodiment, the invention comprises a multi clip device which incorporates fusible links used to connect multiple links with sufficient structural integrity while the device is still able to flex when advanced through a working channel of the endoscope. The fusible links allow the clips to be released and deployed one at a time over the target tissue. According to the invention, the multiple clips are linked in series using semi-rigid fusible links. The links and the clips form a semi rigid clip assembly that allows the chain of clips and the deployment device to maintain flexibility and be able to advance through a tortuous path.

When the operator wants to deploy one of the clips, a mechanism is activated to sever the fusible link between the two most distal clips in the clip assembly. For example, localized heat may be applied to the most distal link in the chain. The heat causes the fusible link to degrade rapidly until the most distal link is free from the chain. At this point the next most distal clip in the series is ready to be deployed using the same procedure, after the distal end of the device is re-positioned over the target tissue.

One exemplary embodiment of the multi clip device according to the invention is shown in FIGS. 6 and 7. The device comprises clips 310, fusible links 308, an actuation wire 320, a heating mechanism 312, a delivery shaft 302 and a power supply interface 326. The distal end of the delivery shaft 302 defines a hollow magazine 304 that contains the clip assembly 306 formed of the clips 310 connected by the fusible links 308.

The clips 310 of the exemplary device are designed to be in a closed position in a resting state, when unaffected by external forces or constraints. The clips 310 may comprise a pair of legs 330 formed from a continuous strip of metal. Opposing jaws 332 may be formed at the ends of the legs 330, capable of compressing the target tissue around the hemostasis site. Since the clips are closed in their natural state, a mechanism is provided to open the clips during deployment, to allow tissue purchase. One exemplary opening mechanism actuates the clip 330 to the open position prior to deployment by forcing the clip's legs 332 to track over pins 350 in the distal end of the delivery shaft 302. The pins 350 act like cams, directing the movement of the legs 332.

Those of skill in the art will understand that the clips 310 may have different geometry that what is shown in the drawings. For example, multi legged clips may be used, and clips that are made of non metallic materials. The device may use clips that are naturally open, and that are closed by a closure mechanism of the delivery shaft 302. For example, pins or cams analogous to those described above may be used to close the clips over the target tissue, and a conventional locking mechanism of the clips may be used to retain the legs 332 in the closed position. One such lock includes a ring which may be slid distally over a clip 310 preventing the legs 332 from moving radially outward toward the open position.

The fusible links 308 connect pairs of successive links 310. The links 308 may be formed of a polymer that allows them to be overmolded onto the proximal end of one clip 310 and the distal end of an adjacent clip 310. The links 310 have a certain amount of flexibility, so that the clip assembly 306 does not become too stiff and prevents the distal end of the delivery shaft 302 from passing through a tortuous path. The fusible links 308 have sufficient compressive strength to allow the series of clips in the clip assembly 306 to be pushed by the actuation wire 320, during advancement of the clips 310 and deployment of the most distal clip 314. As would be understood by those skilled in the art, the fusible links 308 need not be formed as solid members. Rather, these links 308 may be formed as coiled, spring like structures with open or closed surfaces (i.e., with adjacent sections of the coil touching one another or separated longitudinally from one another).

When it is necessary to detach the most distal clip 314 form the adjacent clip 310, the distal fusible link 316 is degraded using localized heating. As the heat is applied to the link 316, it separates from the distal end of the clip 310, located next to the clip 314 being deployed. In this embodiment, the link 316 remains attached to the proximal end of the most distal clip 314 that is deployed, to prevent being lost in the operative area. The link 316 may be manufactured of an electrically conductive plastic, or may comprise a conductive element to direct the heating to a desired portion near the more proximal clip.

In different embodiments, other materials may be used to manufacture the fusible links 308. For example, the links may be metallic, or may be formed of an electroactive polymer so that less heat may be necessary to deploy the clip 310. In the latter embodiment, warm water from the lavage feature of the endoscope may be used instead of a dedicated heating system to release the clip. Instead of degrading the material of the link, using an electroactive polymer would require reshaping the material of the link.

Another embodiment of the link 308 may be manufactured by including elements of shape memory alloys. For example, the link 308 may be constrained to one shape that forms a connection to the clips 310 while within the delivery shaft 302. Once the link 308 is advanced past a selected point at the end of the delivery shaft 302, the constraint is no longer present, and the clip 308 is free to return to its unconstrained, memory state. The memory state may be such that one of the clips 310 attached to the link 308 is released, so that it may be deployed.

In the exemplary embodiment described, the heating mechanism 312 comprises an electrical circuit receiving power form a power supply via an interface 326, which may be a conventional connector. The electrical power is routed to the fusible link 316 by conductive elements, such that the link 316 is destroyed because of the heating generated. A bipolar or a monopolar power supply may be used according to the invention, depending on requirements of the procedure.

According to a further embodiment of the invention, the heating mechanism 312 may be used to direct some heat to the clip 310. An additional therapeutic benefit may be obtained by heating the clip 310, because the hemorrhaging target tissue may be cauterized as well as being mechanically compressed by the clip 310. This aspect of the therapy is beneficial, because cauterization is a preferred method of treatment for peptic ulcer disease.

The actuation wire 320 may be a metallic control wire similar to that described above, having a proximal end actuated from outside the body by an operator using a slide 322 and handle 324 or other type of conventional actuating mechanism as would be understood by those skilled in the art. The actuating mechanism according to this embodiment is preferably designed such that the clips 310 are released by placing the control wire 320 in either compression or tension to push or pull the clips distally, respectively. The control wire 320 is preferably manufactured of an electrically non-conductive material, to keep it insulated from the electrical energy powering the heating mechanism 312.

The delivery shaft 302 according to the invention comprises a flexible metallic coil, similar to the shafts used in biopsy forceps devices. In an exemplary embodiment, the shaft 302 may be coated with a layer of flexible, lubricous material to facilitate insertion through the working channel of an endoscope and minimize the potential for damage to the endoscope. The coating may also be electrically insulative, to protect the operator and the patient from inadvertent electrical shock. In a different embodiment, the shaft 302 may be formed entirely from an electrically non-conductive material with a separate conductive element carrying electrical power to the heating element 312. Alternatively, other heating elements suitable for use with the present invention may include sources of laser energy, ultrasound, RF, etc.

After a patient has been intubated and prepared for the procedure, the delivery shaft 302 is advanced and the power supply is connected to the power supply interface 326. The distal end of the device is then inserted into the body to a desired position adjacent to target tissue (e.g., a site of internal bleeding caused by an ulcer), so that the clip 310 may be deployed on the target tissue.

The user manipulates the actuation wire 320 to advance the clip assembly 306 relative to the shaft 302 and to open the most distal clip 314 in close proximity to the target tissue. Further manipulation of the actuation wire 320 causes the clip 314 to close over the target tissue. At this point, the heating mechanism 312 is energized to release the clip 314 as the link 316 is destroyed. The clip 314 remains locked in position over the target tissue while the delivery device 300 is freed for removal and/or repositioning over a subsequent portion of target tissue. The procedure is repeated to clip other portions of the target tissue as necessary.

The present invention has been described with reference to specific exemplary embodiments. Those skilled in the art will understand that changes may be made in details, particularly in matters of shape, size, material and arrangement of parts. Accordingly, various modifications and changes may be made to the embodiments. The specifications and drawings are, therefore, to be regarded in an illustrative rather than a restrictive sense.

What is claimed is:

1. A clipping device, comprising:
    a shaft defining a lumen therethrough from a proximal end which, during a procedure remains outside the body accessible to a user and a distal end including a distal opening which, during a procedure is inserted into the body to a position adjacent and external to target tissue;
    a flexible clip deployable from the distal opening and configured to assume a shape selected to clip tissue and prevent a flow of fluid therethrough, wherein when residing within the lumen the clip is held substantially straight by an inner diameter of the lumen and when clipping tissue the clip is configured to compress the target tissue without penetrating it;
    a control wire extending through the lumen from the proximal end to the distal end thereof; and
    a release mechanism connecting the control wire to the clip during deployment of the clip and disconnecting the control wire from the clip after deployment thereof.

2. The clipping device according to claim 1, further comprising:
    a control handle coupled to the proximal end of the control wire for operating the release mechanism.

3. The clipping device according to claim 1, wherein the shape of the clip in the unconstrained state is a coiled loop.

4. The clipping device according to claim 1, wherein the release mechanism comprises a failure point defined along the control wire.

5. The clipping device according to claim 4, wherein the failure point is formed as a portion of the control wire having a cross sectional area reduced compared to the rest of the control wire.

6. The clipping device according to claim 1, wherein the control wire comprises first and second portions separate from one another and the release mechanism comprises a bonding agent coupling the first and second portions of the control wire to one another.

7. The clipping device according to claim 1, wherein the release mechanism includes a fusible link formed along the control wire.

8. The clipping device according to claim 1, wherein, in the unconstrained state, the clip is substantially "V" shaped with arms biased toward one another to clip tissue therebetween.

9. The clipping device according to claim 1, wherein the clip moves to the unconstrained state as it exits the distal end of the shaft.

10. The clipping device according to claim 1, wherein the delivery shaft has a maximum outer diameter of approximately 0.1 inches.

11. The clipping device according to claim 10, wherein the delivery shaft is sized and shaped for insertion through a working channel of an endoscope.

12. The clipping device according to claim 1, wherein the clip is rotatable.

13. The clipping device of claim 1, wherein:
    the release mechanism includes an energy delivery element for applying an amount of energy sufficient to disconnect the clip from the control wire.

14. A method for clipping tissue, comprising:
    advancing a distal end of a flexible shaft to a first desired position within the body adjacent and external to a first portion of target tissue to be clipped;
    actuating a control wire extending through the shaft to advance a clip out of the distal end of the shaft over the first portion of target tissue, the clip being biased toward a tissue clipping shape selected to grip tissue received therein wherein, when received within the shaft, the clip is substantially straight;

advancing the clip out of the delivery shaft so that the clip reverts to the tissue clipping shape compressing the first portion of target tissue received therein, the clip compressing the first portion of the target tissue without penetrating the target tissue; and detaching the clip from the control wire.

15. The method according to claim 14, further comprising: twisting the control wire to detach the clip from the control wire.

16. The method according to claim 14, further comprising: heating a link coupling the clip to the control wire to release the clip from the control wire.

17. The method according to claim 14, further comprising: inserting the shaft through a working channel of an endoscope to the first desired position and using a vision system of the endoscope to observe the procedure.

18. The method of claim 14, wherein the step of detaching includes applying an amount of energy sufficient to disconnect the clip from the control wire.

\* \* \* \* \*